(12) United States Patent
Lammertse

(10) Patent No.: US 9,383,832 B1
(45) Date of Patent: Jul. 5, 2016

(54) HAPTIC USER INTERFACE

(71) Applicant: Moog Inc., East Aurora, NY (US)

(72) Inventor: Pieter Lammertse, Amstelveen (NL)

(73) Assignee: Moog Inc., East Aurora, NY (US)

( * ) Notice: Subject to any disclaimer, the term of this patent is extended or adjusted under 35 U.S.C. 154(b) by 78 days.

(21) Appl. No.: 14/218,274

(22) Filed: Mar. 18, 2014

Related U.S. Application Data

(63) Continuation of application No. 13/407,420, filed on Feb. 28, 2012, now Pat. No. 8,716,973.

(60) Provisional application No. 61/447,684, filed on Feb. 28, 2011.

(51) Int. Cl.
| | | |
|---|---|---|
| *G05B 11/01* | (2006.01) | |
| *G06F 3/0346* | (2013.01) | |
| *B25J 9/16* | (2006.01) | |

(52) U.S. Cl.
CPC ............. *G06F 3/0346* (2013.01); *B25J 9/1694* (2013.01); *Y10S 901/14* (2013.01); *Y10S 901/46* (2013.01)

(58) Field of Classification Search
CPC ............................ H05K 5/0017; G05G 9/047
USPC ......... 318/671, 560, 568.21, 690; 700/13, 15, 700/17, 29, 30, 31, 61, 63, 85, 98; 345/179, 345/184; 414/5, 1; 434/263, 262, 264; 702/152, 153, 150, 41
See application file for complete search history.

(56) References Cited

U.S. PATENT DOCUMENTS

| | | | |
|---|---|---|---|
| 2,475,484 | A | 7/1949 | DeNise |
| 2,846,084 | A | 8/1958 | Goertz et al. |
| 3,139,990 | A | 7/1964 | Jelatis et al. |
| 4,012,014 | A | 3/1977 | Marshall |
| 4,046,262 | A | 9/1977 | Vykukal et al. |
| 4,062,455 | A | 12/1977 | Flatau |
| 4,216,467 | A | 8/1980 | Colston |
| 4,221,516 | A | 9/1980 | Haaker et al. |
| 4,398,889 | A | 8/1983 | Lam et al. |
| 4,414,537 | A | 11/1983 | Grimes |

(Continued)

FOREIGN PATENT DOCUMENTS

| | | |
|---|---|---|
| CA | 2172825 | 7/2003 |
| DE | 10217630 | 4/2002 |

(Continued)

OTHER PUBLICATIONS

Adelstein et al.; Design and Implementation of a Force Reflecting Manipulation for Manual Control Research Advances in Robotics; 1992; DSC—vol. 42.

Tadros: Control System Design for a Three Degree of Freedom Virtual Environment Simulator Using Motor/Brake Pair Actuators, Submitted to the Department of Mechanical Engineering at the Massachusetts Institute of Technology, Feb. 1990.

Buchanan; Use of Simulation Technology in Dental Education; Journal of Dental Education—Nov. 2001—vol. 65, No. 11.

Grimaldi et al.; A New Myohaptic Device to Assess Wrist Function in the Lab and in the Clinic—The Wristalyzer; EuroHaptics 2008, LNCS 5024, pp. 33-42, 2008; Springer-Verlag Berlin.

(Continued)

*Primary Examiner* — Rita Leykin
(74) *Attorney, Agent, or Firm* — Phillips Lytle LLP

(57) ABSTRACT

A haptic arm comprising: a user connection element; a reference; a first linkage connecting the user connection element to the reference, where the first linkage provides at least six independent degrees of freedom, and contains an intermediate link, three force sensors, three angle sensors; a second linkage connecting the intermediate link to the reference; a third linkage connecting the intermediate link to the reference a fourth linkage connecting the intermediate link to the reference; the second, third, and fourth linkages each containing an independent actuator and position sensor.

7 Claims, 11 Drawing Sheets

(56) References Cited

U.S. PATENT DOCUMENTS

| | | | |
|---|---|---|---|
| 4,555,960 A | 12/1985 | King | |
| 4,595,334 A | 6/1986 | Sharon | |
| 4,604,016 A | 8/1986 | Joyce | |
| 4,648,782 A | 3/1987 | Kraft | |
| 4,795,296 A | 1/1989 | Jau | |
| 4,819,496 A | 4/1989 | Shelef | |
| 4,874,998 A | 10/1989 | Hollis, Jr | |
| 4,883,400 A | 11/1989 | Kuban et al. | |
| 4,895,039 A | 1/1990 | Hegg | |
| 4,913,000 A | 4/1990 | Wyllie | |
| 4,914,976 A | 4/1990 | Wyllie | |
| 4,950,116 A | 8/1990 | Nishida | |
| 4,988,981 A | 1/1991 | Zimmerman et al. | |
| 5,007,300 A | 4/1991 | Siva | |
| 5,018,922 A | 5/1991 | Yoshinada et al. | |
| 5,019,761 A | 5/1991 | Kraft | |
| 5,024,116 A | 6/1991 | Kraft | |
| 5,038,089 A | 8/1991 | Szakaly | |
| 5,053,975 A | 10/1991 | Tsuchihashi et al. | |
| 5,103,404 A | 4/1992 | McIntosh | |
| 5,142,931 A | 9/1992 | Menahem | |
| 5,143,505 A | 9/1992 | Burdea et al. | |
| 5,146,566 A | 9/1992 | Hollis, Jr. et al. | |
| 5,184,319 A | 2/1993 | Kramer | |
| 5,185,561 A | 2/1993 | Good et al. | |
| 5,193,963 A | 3/1993 | McAffee et al. | |
| 5,255,211 A | 10/1993 | Redmond | |
| 5,266,875 A | 11/1993 | Slotine et al. | |
| 5,350,033 A | 9/1994 | Kraft | |
| 5,354,162 A | 10/1994 | Burdea et al. | |
| 5,382,885 A | 1/1995 | Salcudean et al. | |
| 5,389,865 A | 2/1995 | Jacobus et al. | |
| 5,459,382 A | 10/1995 | Jacobus et al. | |
| 5,576,727 A * | 11/1996 | Rosenberg | G01B 5/008 345/161 |
| 5,625,576 A | 4/1997 | Massie et al. | |
| 5,688,118 A | 11/1997 | Hayka et al. | |
| 5,898,599 A | 4/1999 | Massie et al. | |
| 5,929,846 A * | 7/1999 | Rosenberg | G01B 5/008 345/156 |
| 6,028,409 A | 2/2000 | Wierda | |
| 6,037,927 A | 3/2000 | Rosenberg | |
| 6,088,020 A | 7/2000 | Mor | |
| 6,191,796 B1 | 2/2001 | Tarr | |
| 6,323,837 B1 | 11/2001 | Rosenberg | |
| 6,405,158 B1 | 6/2002 | Massie et al. | |
| 6,654,000 B2 | 11/2003 | Rosenberg | |
| 6,853,965 B2 | 2/2005 | Massie et al. | |
| 6,929,481 B1 * | 8/2005 | Alexander | G09B 23/285 434/262 |
| 7,103,499 B2 * | 9/2006 | Goodwin | G06F 3/016 318/568.11 |
| 7,215,326 B2 | 5/2007 | Rosenberg | |
| 7,225,115 B2 | 5/2007 | Jones | |
| 7,233,313 B2 * | 6/2007 | Levin | G06F 3/016 345/156 |
| 7,249,952 B2 * | 7/2007 | Ranta | G09B 23/283 434/263 |
| 7,460,104 B2 * | 12/2008 | Rosenberg | A63F 13/06 345/156 |
| 7,480,600 B2 | 1/2009 | Massie et al. | |
| 7,489,309 B2 * | 2/2009 | Levin | G06F 3/016 345/156 |
| 7,543,588 B2 * | 6/2009 | Wang | A61B 17/00 128/898 |
| 7,573,461 B2 | 8/2009 | Rosenberg | |
| 7,753,461 B2 * | 7/2010 | Leistner | B60N 3/104 108/27 |
| 8,108,190 B2 * | 1/2012 | Riener | G09B 23/32 434/267 |
| 2002/0119432 A1 | 8/2002 | Ranta et al. | |
| 2003/0034994 A1 | 2/2003 | Massie et al. | |
| 2004/0091845 A1 * | 5/2004 | Azerad | G09B 23/283 434/263 |
| 2006/0019228 A1 | 1/2006 | Riener et al. | |
| 2008/0046226 A1 | 2/2008 | Massie et al. | |

FOREIGN PATENT DOCUMENTS

| | | |
|---|---|---|
| DE | 69430751 | 3/2003 |
| EP | 0721615 | 6/2002 |
| EP | 1500067 | 1/2005 |
| GB | 2288686 | 10/1995 |
| JP | 9503603 | 4/1997 |
| JP | 2007193848 | 8/2007 |
| JP | 2009148888 | 7/2009 |
| WO | 9628800 | 9/1996 |
| WO | 9917265 | 4/1999 |
| WO | 9939317 | 8/1999 |
| WO | 9942978 | 8/1999 |
| WO | 03090179 A3 | 10/2003 |

OTHER PUBLICATIONS

Brooks et al.; Project GROPE—Haptic Displays for Scientific Visualization; Computer Graphics, Aug. 1990, vol. 24, No. 4.

Harris; How Haptic Technology Works; Web page—http://electronics.howstuffworks.com/gadgets/other-gadgets/haptic-technology3.htm; Printed Apr. 13, 2009.

Grimaldi et al.; Effects of Inertia and Wrist Oscillations on Contralateral Neurological Postural Tremor Using the Wristalyzer, a New Myohaptic Device; IEEE Transactions on Biomedical Circuits and Systems, Dec. 2008, vol. 2, No. 4.

Johnson et al.; An Initial Evaluation of the Iowa Dental Surgical Simulator; Journal of Dental Education—Dec. 2000—vol. 64, No. 12.

SensAble Technologies; The SensAble Dental Lab System; 2008.

Lammertse; Novelty of MOOG Dental Training Device; Mar. 10, 2009.

Van Der Linde; The HapticMaster, A New High Performance Haptic Interface; 2002; FCS Control Systems, The Netherlands.

Salisbury et al.; The Fourth PHANTOM Users Group Workshop AI Laboratory Technical Report No. 1675 R.L.E. Technical Report No. 633; Nov. 1999.

Hannaford et al.; Performance Evaluation of a Six-Axis Generalized Force-Reflecting Teleoperator; IEEE Transactions on Systems, Man, and Cybernetics, May/Jun. 1991, vol. 32, No. 3.

SensAble Technologies Website; About Us; 2009.

SensAble Technologies Desktop; Specifications for the PHANTOM Desktop and PHANTOM Omni haptic devices; Jan. 2009.

Manto et al.: Unraveling of an Original Mechanism of Hypometria in Human Using a New Myohaptic Device—The Wristalyzer; ECIFMBE 2008, IFMBE Proceedings 22, pp. 1646-1649, 2008; www.springerlink.com © Springer-Verlag Berlin Heidelberg 2009.

Reiley et al..: Effects of Visual Force Feedback on Robot-Assisted Surgical Task Performance. The Journal of Thoracic and Cardiovascular Surgery, pp. 196 -202, Jan. 2008.

Hogan: Impedance Control: An Approach to Manipulation: Part I—Theory, Journal of Dynamic Systems, Measurement and Control, Mar. 1985, vol. 107.

Hogan: Impedance Control: An Approach to Manipulation: Part II—Implementation, Journal of Dynamic Systems, Measurement and Control, Mar. 1985, vol. 107.

Hogan: Impedance Control: An Approach to Manipulation: Part III—Applications, Journal of Dynamic Systems, Measurement and Control, Mar. 1985, vol. 107.

Massie: Design of a Three Degree of Freedom Force-Reflecting Haptic Interface, Submitted to the Department of Electrical Engineering and Computer Science at the Massachusetts Institute of Technology, May 1993.

Russo: The Design and Implementation of a Three Degree of Freedom Force Output Joystick, Submitted to the Department of Mechanical Engineering at the Massachusetts Institute of Technology, May 1990.

* cited by examiner

HAPTIC USER INTERFACE

TECHNICAL FIELD

The technical field relates to haptic interfaces, and more specifically to a haptic user interfaces which senses forces applied by a user to a haptic tool, and which controls the position of the haptic tool in response to the user's applied forces.

BACKGROUND ART

Force feedback systems are generally known. For example, U.S. Patent Publication No. 2004/0091845 entitled "System and Method for Virtual Reality Training for Odontology" is directed to a training system for odontology in which the spacial position of a hand-held element is sensed, a three-dimensional representation of a virtual object is displayed on a display screen, and a virtual instrument is provided for operating on the virtual object. Force feedback is provided to the hand held element when the virtual instrument interacts with the virtual object.

U.S. Pat. No. 5,587,937 entitled "Force Reflecting Haptic Interface" is directed to a force feedback system having a thimble-like user connection element for physically exchanging a force with the user. The system provides at least three powered degrees of freedom and at least one independent degree free of power.

U.S. Pat. No. 6,028,409 entitled "Control System for Telemanipulation" is directed to a remote control system having two circuits each containing an actuator acting on a mass and controlled by an actuator signal. A manual control means having a force transducer and velocity transducer is attached to each actuator. Each circuit contains a control circuit representing a model of the dynamics of a moving mass in which an input from the other circuit is divided by a simulated mass to obtain a commanded acceleration signal which is time integrated to obtain a commanded velocity signal which is provided to the respective actuator.

BRIEF SUMMARY OF THE INVENTION

With parenthetical reference to the corresponding parts, portions or surfaces of the disclosed embodiment, merely for the purpose of illustration and not by way of limitation, a haptic arm (230) is provided comprising a user connection element (242), a reference (L19), a first linkage connecting the user connection element to the reference, the first linkage providing at least six independent degrees of freedom between the user connection element and the reference, the first linkage comprising an intermediate link (L15), three force sensors (F1, F2, F3) for sensing forces applied by a user (210) to the user connection element in three dimensions and three angle sensors (R1, R2, R3) arranged to sense the three dimensional orientation of the user connection element relative to the intermediate link, a second linkage connecting the intermediate link to the reference, the second linkage providing power to a first powered degree of freedom through a first actuator (A1), the second linkage comprising a position sensor (R4) arranged to measure the first powered degree of freedom, a third linkage connecting the intermediate link to the reference, the third linkage providing power to a second powered degree of freedom through a second actuator (A2), the third linkage comprising a position sensor (R5) arranged to measure the second powered degree of freedom, and a fourth linkage connecting the intermediate link to the reference, the fourth linkage providing power to a third powered degree of freedom through a third actuator (A3), the fourth linkage comprising a position sensor (R6) arranged to measure the third powered degree of freedom.

The actuators may be mounted on the reference. The actuators may be electric motors. The force sensors may be strain gauges and the angle sensors may be potentiometers, resolvers or encoders. Each of the force sensors may be mounted on a force sensing link, the force sensing link comprising openings (263a, 263b, 263c) adjacent each strain gauge and arranged to amplify the strain sensed by each respective strain gauge. The force sensing link and the intermediate link may be the same. The linkages may be configured such that gravity does not cause a significant torque on any of the actuators when the user connection element is in a starting position.

In another aspect, a user interface (200) is provided comprising a reference (L19), a first tool interface (230) having a first tool handle (242) with at least three independent translational degrees of freedom and three independent orientation degrees of freedom between the first tool handle and the reference, the first tool interface comprising three force sensors (F1, F2, F3) for measuring forces applied by a user (210) to the first tool interface along the three independent translational degrees of freedom, three orientation sensors (R1, R2, R3) for measuring the three independent orientation degrees of freedom and three actuators (A1, A2, A3) for controlling the position of each of the three independent translational degrees of freedom, a second tool interface (250) having a second tool handle (253) with at least six independent degrees of freedom between the second tool handle and the reference, the second tool handle interface comprising three position sensors (251) and three orientation sensors (252) for measuring the six independent degrees of freedom between the second tool handle and the reference, a video display (240) arranged to produce a stereoscopic view co-located with the first tool handle and second tool handle, a computer system (270) comprising a three dimensional virtual environment (401), the three dimensional virtual environment comprising a first virtual tool (442) having a first virtual position and a first virtual orientation, a second virtual tool (450) having a second virtual position and a second virtual orientation, and at least one virtual object (471) having a third virtual position and a third virtual orientation, the computer system programmed to adjust the virtual position of the first virtual tool as a function of the first tool interface force sensors, and to adjust the virtual position of the second virtual tool as a function of the second tool interface position sensors and orientation sensors, the computer system programmed to control the actuators such that the position of the first tool handle is adjusted to correlate to changes in the position of the first virtual tool, the computer system programmed to provide the video display with images of the virtual environment.

The computer system may be programmed to detect collisions (341) between the first virtual tool and the virtual object and the adjustment of the first virtual position of the first virtual tool may be a function of the collisions at a first frequency. The virtual object may comprise a voxel model (382). The voxel model may comprise multiple voxel elements and each of the voxel elements may comprise a hardness parameter and a stiffness parameter. The virtual object may comprise a mesh model (379). The virtual object may comprise a virtual tooth model having finite elements and each element may comprise a tooth material type parameter. The tooth material type parameter may be selected from a group consisting of a cavity, dentin, pulp and enamel.

The first virtual tool may comprise a modification region or an interaction region (342). The computer system may calculate an interaction force (341) between the first virtual tool and the virtual object as a function of the interaction region, the first virtual tool position (327) and the virtual object position. The interaction force may be a function of a virtual object voxel element stiffness parameter. The first virtual tool may comprise a virtual mass (322) and the computer system may be programmed to accelerate the first virtual tool with an acceleration generally equal to the force sensors outputs summed (321) with the interaction force, and divided by the virtual mass. The virtual object may be modified as a function of the position of the modification region relative to the virtual object position. The virtual object may be modified as a function of the interaction force.

The user interface may further comprise a foot pedal (256) and the foot pedal may comprise a position sensor and/or a bias spring. The virtual object may be modified as a function of the position sensor in the foot pedal. The second virtual tool may comprise a virtual mirror surface. The user interface may further comprise a speaker (241).

The user interface may further comprise a servo control module (360) arranged to control the actuators as a function of the position of the first virtual tool. The computer system may be programmed to detect collisions (341) between the first virtual tool and the virtual object, the adjustment of the first virtual position of the first virtual tool may be a function of the collisions at a first frequency, and the servo control module may operate at a frequency greater than the first frequency. The first tool interface may further comprise three position sensors (245) and three tachometer sensors (261) and the servo control module may be configured to adjust its output as a function of the position sensors and tachometer sensors. The servo control module may comprise a kinematic model of the linkages.

The video display may be configured to alternatively display left eye images and right eye images. The video display may be configured to simultaneously display left eye images at a first polarization and right eye images at a second polarization. The video display may be configured to display images of dental tools which may be true to scale.

In another aspect, a method of simulating a virtual dental surgery is provided comprising the steps of providing a first tool interface having a first tool handle with at least three independent translational degrees of freedom and three independent orientation degrees of freedom between the first tool handle and a reference, the first tool interface comprising three force sensors for measuring forces applied to the first tool interface along the three independent translational degrees of freedom, three orientation sensors for measuring the three independent orientation degrees of freedom, and three actuators for controlling the position of each of the three independent translational degrees of freedom, providing a second tool interface having a second tool handle with at least six independent degrees of freedom between the second tool handle and the reference, the second tool handle interface comprising three position sensors and three orientation sensors for measuring the six independent degrees of freedom between the second tool handle and the reference, providing a video display (240) arranged to produce a stereoscopic view co-located with the first tool handle and second tool handle, providing a three dimensional virtual environment comprising a first virtual tool having a first virtual position and a first virtual orientation, a second virtual tool having a second virtual position and second virtual orientation, and at least one virtual object having a third virtual position and third virtual orientation, adjusting the virtual position of the first virtual tool as a function of the first tool interface force sensors, adjusting the virtual position of the second virtual tool as a function of the second tool interface position sensors and orientation sensors, controlling the actuators such that the first tool handle is adjusted to correlate to changes in the virtual position of the first virtual tool, and providing the video display with images of the virtual environment.

The function may comprise accelerating the first virtual tool within the virtual environment in proportion to an output of the three force sensors. The step of controlling the actuators may comprise using a PID. The second virtual tool may be a virtual mirror. The virtual object may comprise a triangular mesh. The first virtual object may comprise an interaction region defined by an analytic function. The method may further comprise the step of detecting a collision between the first virtual tool interaction region and the virtual object. The method may further comprise the step of calculating an interaction force as a function of the collision and accelerating the first virtual tool as a function of the interaction force. The method may further comprise the step of modifying the virtual object as a function of the collision. The method may further comprise the step of providing a foot pedal interface having at least one degree of freedom. The step of modifying the virtual object may be a function of the foot pedal interface.

DESCRIPTION OF THE PREFERRED EMBODIMENTS

Figure 1:
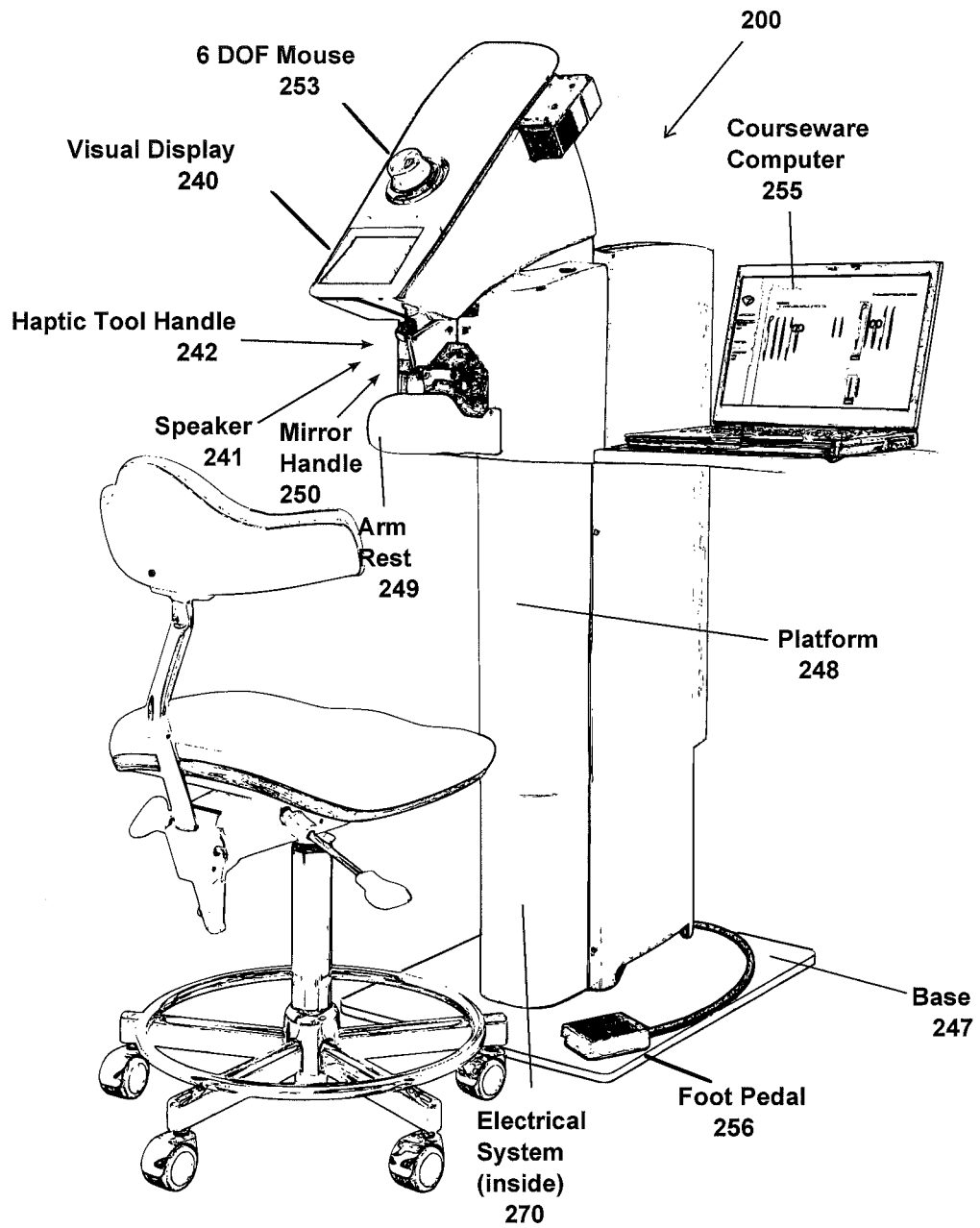
FIG. 1 is an isometric view of a first embodiment of the user interface system.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Referring now to the drawings, and more particularly to FIG. 1, this invention is directed to a haptic user interface system, a first embodiment of which is generally indicated at 200. As shown, dental surgery simulator system 200 generally includes haptic tool 242, in this embodiment a dental drill handle, visual display 240, input stylus 250, in this embodiment a dental mirror handle, foot pedal 256, six degree of freedom mouse 253, electrical system 270, speaker 241, and courseware computer 255. System 200 is structurally supported by platform 248.

User 210 interacts with system 200 by applying forces to haptic dental drill handle 242. Additionally, user 210 provides input to system 200 through dental mirror stylus 250, six degree of freedom mouse 253, and foot pedal 256. Sensors within system 200 detect the position and orientation of haptic tool handle 242, stylus 250, six degree of freedom mouse 253, and foot pedal 256.

Figure 2:
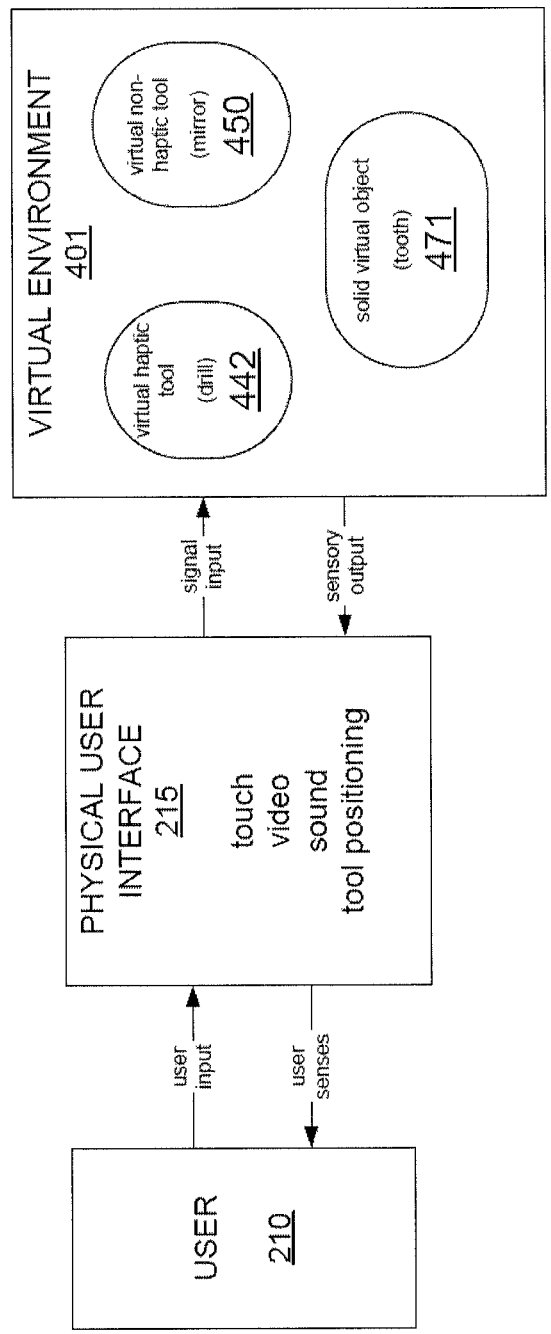
FIG. 2 is an object diagram of the user interface system shown in FIG. 1.

As shown in FIG. 2, virtual environment 401 includes virtual haptic tool 442, in this embodiment a dental drill corresponding to real world haptic drill handle 242, and virtual non-haptic tool 450, in this embodiment a dental mirror corresponding to real world dental mirror handle 250. Virtual environment 401 also includes at least one virtual object, such as a virtual tooth 471, all of which are viewed by user 210 in display 240.

The position of virtual drill 442 is adjusted in response to the forces user 210 applies to haptic drill handle 242 and the interaction of virtual drill 442 with virtual teeth 471. More specifically, virtual environment 401 includes algorithms for determining how virtual drill 442 should move in response to the sum of the x,y,z forces applied by user 210 on drill handle 242 and any reaction forces from virtual contact of virtual haptic tool 442 with virtual teeth 471. Virtual environment 401 generally uses Newtonian physics (i.e. Force=mass×acceleration; Force=spring constant×deflection) to model the movement of virtual drill 442 and the reaction forces between virtual drill 442 and virtual teeth 471. Virtual drill 442 is assigned a virtual mass, and virtual teeth 471 are assigned a hardness and rigidity. The rigidity correlates to the spring constant a tooth provides when contacted and the hardness correlates to how much work virtual drill 442 must do in order to drill away a volume of virtual tooth 471. The position of virtual drill 442 is generally accelerated by the forces applied by user 210 divided by the virtual mass (virtual acceleration=user force/virtual mass). The algorithmic details of how virtual environment 401 operates are described in greater detail below.

Once virtual environment 401 calculates how virtual drill 442 will move, it commands the actuators in system 200 to change the real world position of haptic drill handle 242. User 210 senses the change in position of haptic drill handle 242. While the position of drill handle 242 position is controlled by simulator 200, the orientation of drill handle 242 is controlled by user 210. System 200 measures the orientation of drill handle 242 as controlled by user 210, and in response updates the orientation of virtual drill 442 in virtual environment 401.

Unlike haptic drill handle 242, whose real world position is controlled by simulator 200, the real world position of dental mirror 250 is controlled by user 210. Further, the position and movement of virtual dental mirror 450 is adjusted to directly match the real world position of dental mirror stylus 250. Thus, movement of virtual dental mirror 450 does not follow Newtonian motion in virtual world 401. Additionally, collisions are not calculated between virtual dental mirror 450 and other virtual tools or virtual objects by system 200.

The position and orientation of foot pedal 256 and six degree of freedom mouse 253 are also under direct control of user 210. Foot pedal 256 controls the speed of virtual drill 442. Six degree of freedom mouse 253 is used to adjust the three dimensional camera view of virtual environment 401 shown in display 240. The camera view can be rotated, paned, and zoomed.

Courseware computer 255 provides an interface to the user for selecting different virtual environments to be simulated in the haptic user interface system and running various training software applications. Training applications can monitor the interaction of user 210 with virtual environment 401 and haptic drill handle 242 and measure various criteria to evaluate the performance of user 210.

Figure 3:
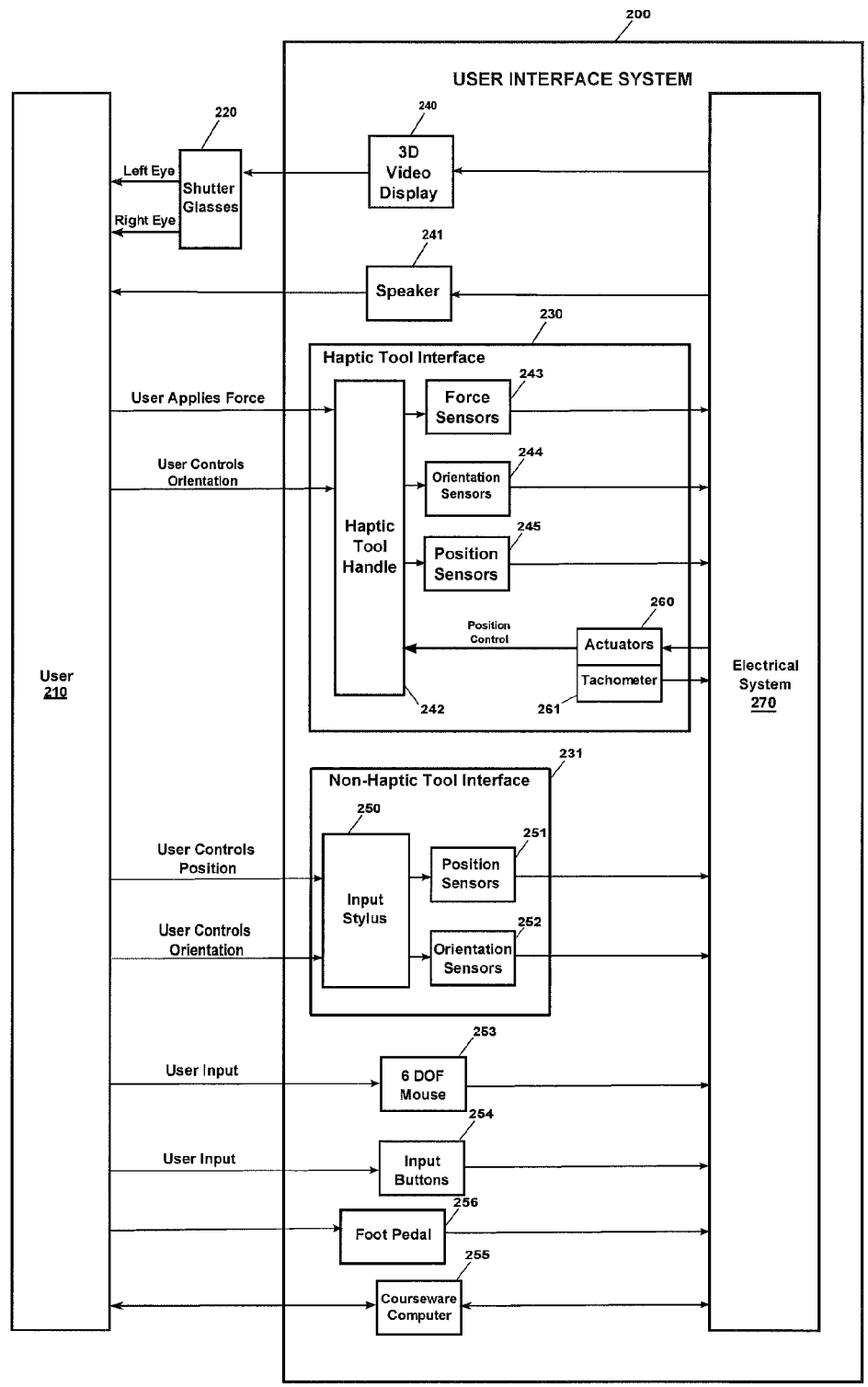
FIG. 3 is a system diagram of the user interface system.

FIG. 3 shows a high level system diagram of the user interface of dental surgery simulator system 200. System 200 provides audio, visual, and haptic sensory information to user 210 through speaker 241, visual display 240, and the positioning of haptic dental drill handle 242. System 200 receives input from user 210 through user 210's interaction with dental drill 242, dental mirror handle 250, six degree of freedom mouse 253, buttons 254, and foot pedal 256. System 200 is also able to provide and receive information with user 210 through courseware computer 255. System 200 contains electrical system 270, which handles a majority of the simulator's processing.

In this embodiment visual display 240 is a color mini LCD display with a frame rate of 120 Hz. A video signal is provided to visual display 240 from electrical system 270. Visual display 240 alternately displays images for the left and the right eye of user 210. User 210 wears shutter glasses 220, which sequentially block light from passing into the left and the right eye. Shutter glasses 220 include synchronization hardware to ensure that the left lens of shutter glasses 220 is blocked when display 240 is displaying a right eye image, and the right lens is blocked when display 240 is displaying a left eye image. User 210 effectively ends up receiving only the left images in her left eye, and only the right images in her right eye, with a frame rate of 60 Hz in each eye.

Visual display 240 is positioned such that the view is co-located with the position of dental tool handle 242 and dental mirror handle 250. This allows system 200 to produce images of virtual dental drill 442 and virtual dental mirror 450 that line up in the line of sight of user 210 with real world dental tool handle 242 and dental mirror handle 250. Shutter glasses 220 may additionally contain convex lenses in front of each eye to adjust the eye lens accommodation level of user 210. For example, the focal length of the convex lenses is selected such that the eye lenses of user 210 adjust their optical power to a power that is consistent with normal viewing of an object at a distance of dental drill handle 242 when the eyes of user 210 are actually focused on visual display 240.

Speaker 241 receives its signal from electrical system 270. Speaker 241 has a dynamic range of 20 Hz-20 kHz, and is positioned close to dental drill handle 242. Electrical system 270 is configured to provide speaker 241 with an audio signal representative of sounds made by a dental drill.

As shown in FIG. 3, haptic tool interface 230 includes dental drill handle 242, force sensor group 243 (F1, F2, F3), orientation sensor group 244 (R1, R2, R3), position sensor group 245 (R4, R5, R6), actuator group 260 (A1, A2, A3), and tachometer group 261 (T1, T2, T3), as well as a number of links and link joints. Force sensors within group 243 are arranged to measure the forces applied to haptic dental drill handle 242 by user 210 generally in the three orthogonal translational axes (x, y, z). Orientation sensors within group 244 are arranged to measure the roll, pitch and yaw axis orientation of dental tool handle 242. Position sensors within group 245 are arranged to measure the translational position (x, y, z) of tip 271 of dental tool handle 242.

Figure 4:
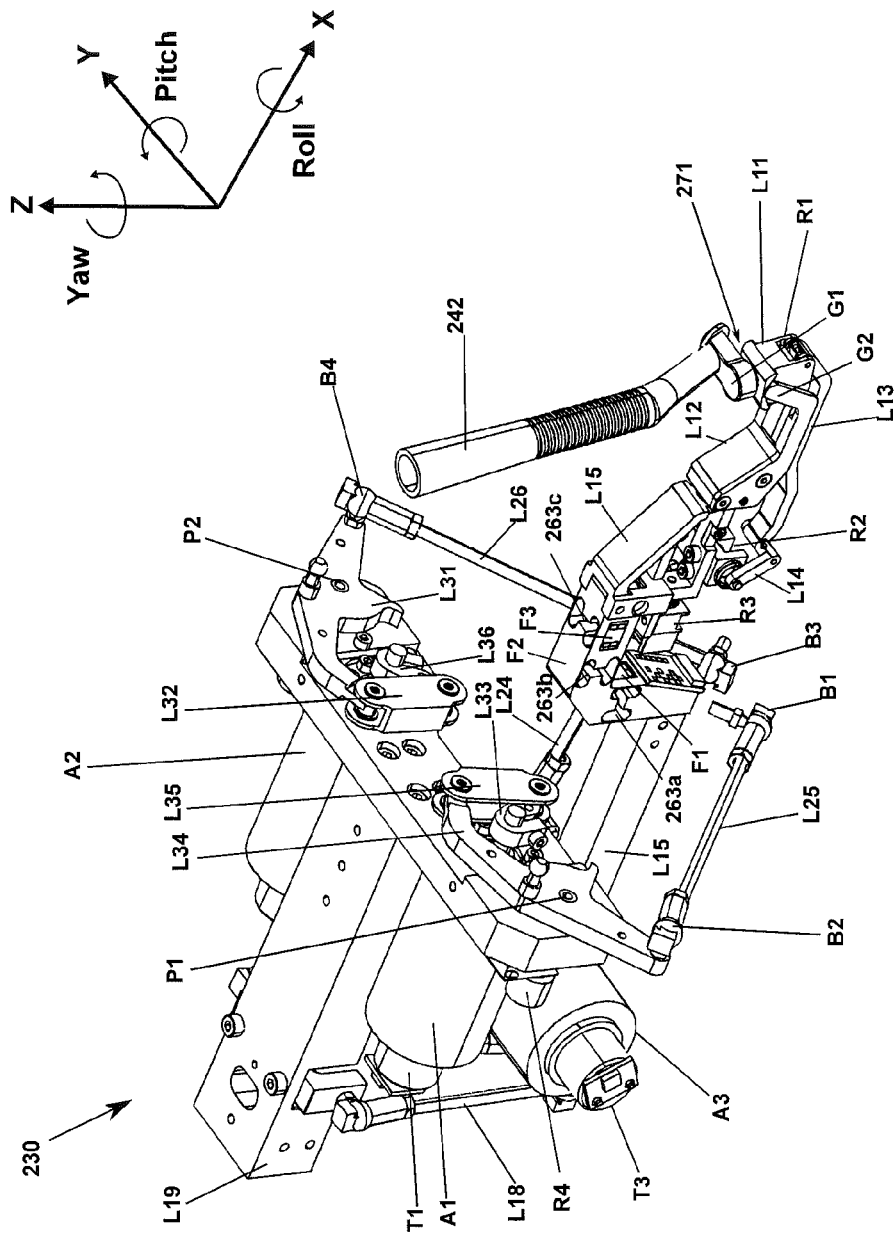
FIG. 4 is an isometric view of the haptic tool interface shown in FIG. 1.
Figure 5:
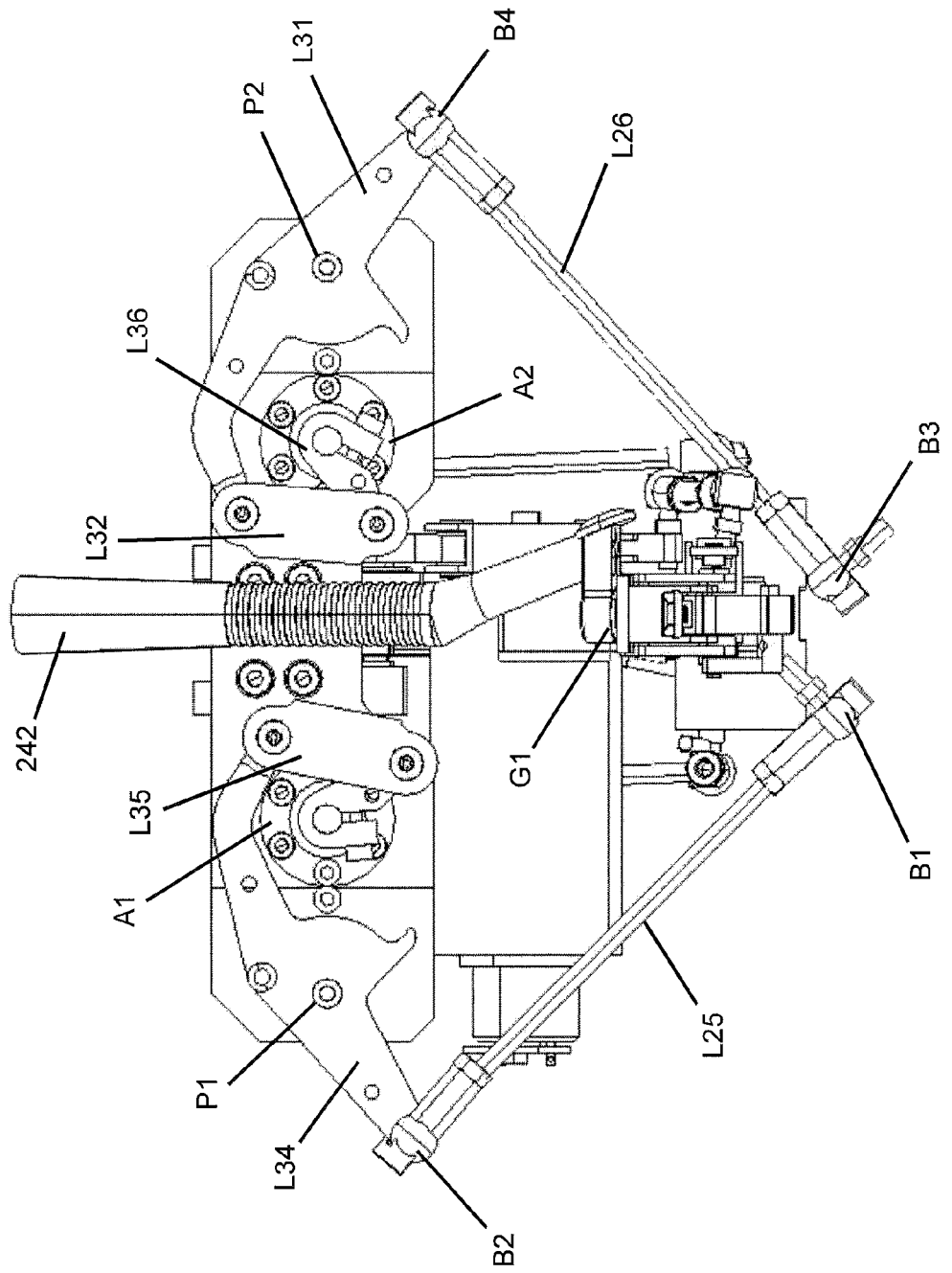
FIG. 5 is a front view of the haptic tool interface shown in FIG. 4.
Figure 6:
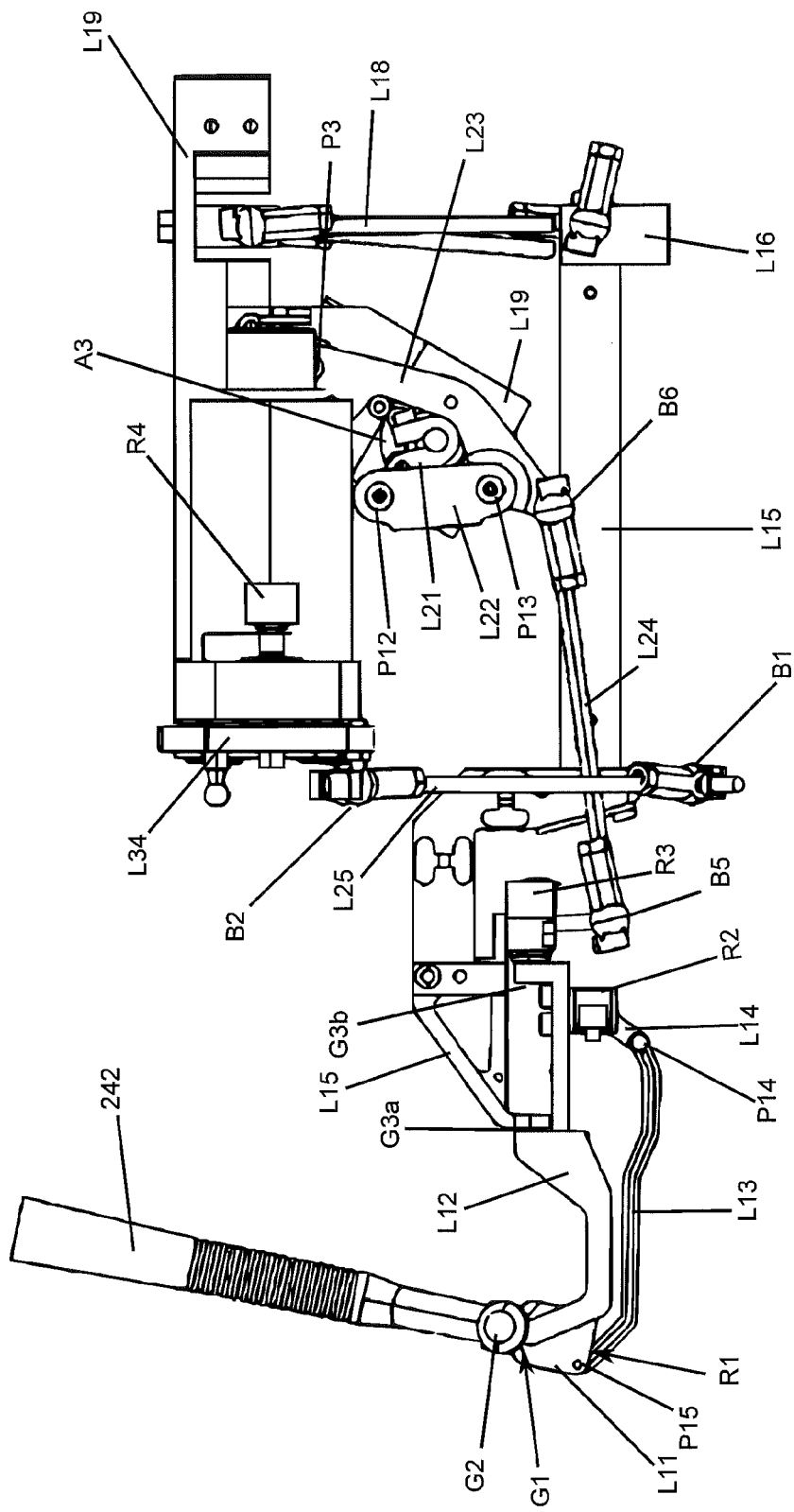
FIG. 6 is a right side view of the haptic tool interface shown in FIG. 4.

FIGS. 4-6 show isometric, front and side views, respectively, of haptic tool interface 230. Haptic tool interface 230 provides six degrees of freedom between the system ground and haptic dental tool handle tip 271. The three translational degrees of freedom (x, y, z) are powered by actuator group 260, which comprises actuators A1, A2 and A3. As shown, haptic tool interface 230 is made up of a number of links interconnected through hinge joints or ball joints. The sensors within orientation sensor group 244 and position sensor group 245 are located at particular hinge joints in haptic tool interface 230.

Grounded link L19 is rigidly coupled to system base 247. All three actuators A1, A2 and A3 are mounted on grounded link L19. Actuators A1, A2 and A3 are permanent magnet electric motors with planetary reduction gears incorporated along their output shafts. Actuators A1, A2 and A3 may alternatively be implemented with direct drive torque motors, rotary hydraulic actuators, variable reluctance motors, or other similar actuators. On the output shaft of each of actuators A1, A2 and A3 are tachmometers T1, T2 and T3 in tachometer group 261. Tachometers T1, T2 and T3 directly measure output shaft rotation speed and provide the measurements to electrical system 270.

Four groups of linkages extend from grounded link L19 to shared link L15: a first linkage group extending from actuator A1, a second linkage group extending from actuator A2, a third linkage group extending from actuator A3, and a fourth linkage group not connected to any actuator. Dental drill handle 242 connects to shared link L15 through a triple gimbal linkage providing three rotational degrees of freedom. The links in haptic tool interface 230 are constructed of a strong light-weight material such as aluminum or titanium.

The first linkage group between L19 and L15 begins with grounding link L19 connecting to link L18 through pivot joint P4, which has an axis of rotation parallel to the y-axis. Link L18 then connects to short link L16 through pivot joint P5, which also has an axis of rotation parallel to the y-axis. Link L16 then connects to shared link straight portion L15a through pivot joint P6, whose axis of rotation is orthogonal to axis of rotation of P5 and generally parallel to the z-axis. First linkage group provides three degrees of freedom between grounded link L19 and shared link L15. Within a limited space, shared link L15 may be moved to any translational (x,y,z) position. While the orientation of shared link L15 changes as its x, y and z positions are moved, the roll, pitch and yaw orientations of shared link L15 are not linearly independent of the x, y, z positions.

The second linkage group between L19 and L15 begins with actuator A1's shaft rotationally coupled to link L33 with an axis of rotation parallel to the x-axis. Link L33 connects with link L35 through pivot joint P7. Link L35 connects to link L34 through pivot joint P8, and link 34 connects back to grounded link L19 through pivot joint P1. Pivot joints P7, P8 and P1 all have their axis of rotation parallel to the x-axis. Link L34 has one degree of freedom which is controlled by actuator A1. L34 connects to link L25 through ball joint B2, and link L25 connects to shared link L15 through ball joint B1. As shown in FIG. 4, angular position sensor R4 is arranged within the second linkage group along pivot joint P1.

Again, the first linkage group creates three degrees of freedom between grounded link L19 and shared link L15. By connecting second linkage group between grounded link L19 and shared link L15, one of the degrees of freedom between grounded link L19 and shared link L15 is under the control of actuator A1. Note that the degree of freedom controlled by actuator A1 is not linear with the x, y or z-axis.

The lengths of links L33, L35, L34, and the position of pivot point P1 are selected to produce a varying mechanical advantage between actuator A1 and the rotation of link L34 such that a generally uniform torque from actuator A1 causes a generally uniform force to be applied from grounded link L19 to shared link L15 throughout the space of normal operation of shared link L15.

The third linkage group between L19 and L15 is a mirror xz-plane of the second linkage group. More specifically, actuator A2, link L36, pivot joint P10, link L32, pivot joint P11, link L32, pivot point P2, ball joint B4, link L26, and ball joint B3 correspond to second linkage group's actuator A1, link L33, pivot joint P7, linkage L35, pivot joint P8, linkage L34, pivot P1, ball joint B2, link L25, and ball joint B3.

Just as the second linkage group controls one of the degrees of freedom between shared link L15 and grounded link L19, the third linkage group controls a second degree of freedom between shared link L15 and grounded link L19. Together, actuators A1 and A2 generally control the yz position of shared link L15.

The fourth linkage group between grounded link L19 and shared link L15 is most clearly shown in the side view of FIG. 6. Actuator A3, which is mounted to grounded link L19, is rotationally coupled to link L21 through actuator A3's output shaft. Link L21 connects to link L22 through pivot joint P12. Link L22 is connected to link L23 through pivot joint P13 and link L23 is connected to grounded link L19 through pivot joint P3. The axis of rotation of actuator A3's output shaft and pivot joints P12, P13 and P3 are all parallel to the y-axis. Link L23 is connected to link L24 through ball joint B6. Link L24 is connected to shared link L15 though ball joint B5. As shown in FIG. 5, arranged within the fourth linkage group along pivot joint P3 is angular position sensor R6. Actuator A3 generally controls the x-location of shared link L15.

Working together, actuators A1, A2, and A3 control the three translational degrees of freedom of shared link L15 relative to grounded link L19.

Shared link portion L15 contains three force sensors F1, F2, F3 arranged along its surface. Force sensors F1, F2, F3 are implemented as strain gauges. Alternatively, force sensors F1, F2, F3 may be piezo-electric load cells, resistive touch sensors, or other similar sensors. As shared link L15 undergoes strain due to forces applied by user 210 to dental handle L15, strain gauges F1, F2, F3 are deformed and produce an electrical output signal change which is sensed by electrical system 270.

Strain enhancing holes 263a, 263b and 263c are placed adjacent to each strain gauge F1, F2 and F3, respectively, in order to decrease the stiffness of portions of shared link L15 and to increase the sensitivity of strain gauges F1, F2 and F3 relative to a link without such openings.

Dental drill handle 242 is attached to shared link L15 through a triple gimbal linkage providing three rotational degrees of freedom (roll, pitch, yaw). The three axes of rotation all intersect at attachment point 271, where dental drill handle 242 attaches to link L11. The triple gimbal linkage between shared link L15 and dental drill handle 242 begins with shared link L15 connecting to link L12 through gimbal pivot joint G3a and G3b. G3 has an axis of rotation generally parallel to the x-axis. Link L12 is connected to link L11 through gimbal pivot joint G2. G2 has an axis of rotation which is generally parallel to the y-axis when dental tool handle 242 is in the default position shown in FIG. 5. Link L11 connects to dental tool handle 242 through attachment point 271, which coincides with gimbal pivot joint G1. Gimbal pivot joint G1 has an axis of rotation generally parallel to the z-axis when dental tool handle 242 is in the default position. Attachment point 271 is configured to allow rapid detachment and reattachment of various different tool handles or interfaces other than dental drill handle 242. Such alternate handles may include a dental pick handle, a dental mirror handle, a dental probe handle, an excavator handle, a burnisher handle, a plugger handle, a forceps handle, a scalpel handle, or various other similar tool handles.

Orientation sensors R1, R2 and R3 are angle sensors, such as a resolver, encoder, variable potentiometer, or other similar device arranged within the linkages between shared link L15 and dental drill handle 242. A supplementary linkage exists between link L12 and link L11 through link L13 in order to provide mechanical input to orientation sensor R2. The supplementary linkage between L12 and L11 begins with orientation sensor R2, which is mounted on link L12. The rotational shaft of orientation sensor R2 connects to link L14. Link L14 connects to link L13 through pivot joint P14. Link L13 then connects to link L11 through pivot joint P15. Orientation sensor R2's rotational axis, as well as the rotational axes of pivot joints P14 and P15, are all parallel to each other, and generally parallel to the y-axis.

Orientation sensor R1 is arranged along gimbal pivot joint G1, and orientation sensor R3 is arranged between links L15 and L12 along gimbal pivot joint G3's axis. Orientation sensor R1 generally measures the yaw angle of dental drill handle 242, orientation sensor R2 generally measures the pitch angle of handle 242, and orientation sensor R3 generally measures the roll angle of handle 242. Each orientation sensor 244 will not be exactly aligned with the x, y and z axes as the dental tool handle is moved or rotated.

Position sensors R4, R5 and R6 are also angle sensors, such as a resolver, encoder, variable potentiometer, or other similar device, arranged within the linkages between shared link L15 and dental drill handle 242. The combined outputs of position sensors R4, R5 and R6 provide the translational position of shared link L15, or triple gimbal point.

Figure 7:
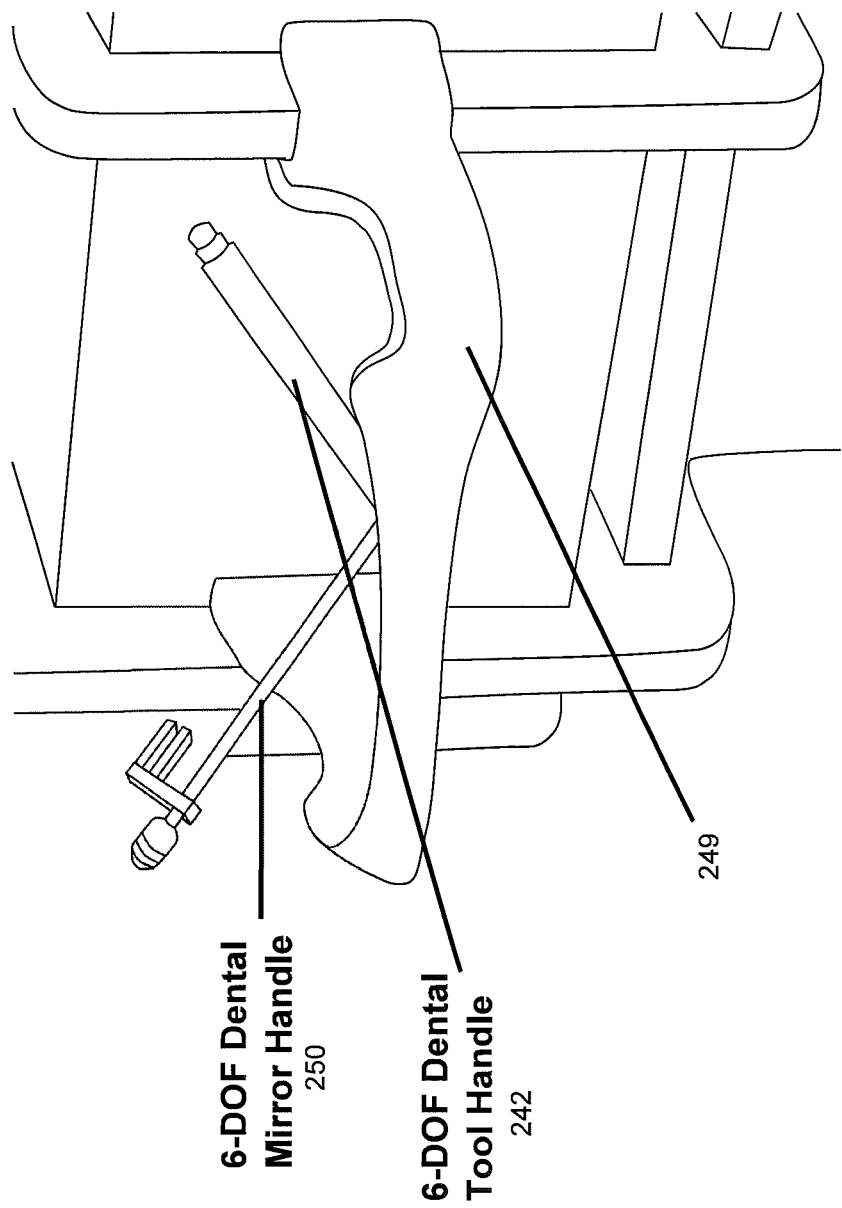
FIG. 7 is an enlarged view of the haptic tool handle and six degree of freedom mouse shown in FIG. 1.

As shown in FIG. 7, dental mirror handle 250 is connected to platform 248 through a mirror linkage. The linkage provides six independent degrees of freedom, including three translational degrees of freedom (x, y, z) and three rotational degrees of freedom (roll, pitch, yaw). Dental mirror orientation sensors 252 and position sensors 251 are arranged within the mirror linkage in a manner similar to the arrangement of haptic tool orientation sensors 244 and position sensors 245 within the haptic tool linkages. The outputs of dental mirror orientation sensors 252 and position sensors 251 are provided to electrical system 270. The mirror linkage is not actively powered. Because dental mirror is not expected to exchange large forces with user 210, it can be constructed from much lower weight materials. Because of the mirror linkage's light weight, user 210 is able to freely move the dental mirror. User arm rest 249 is arranged such that user 210 may reset his/her arms on it while moving the dental mirror handle 250 or providing force to dental drill handle 242.

As shown in FIG. 1, foot pedal 256 is arranged along the floor in front of platform 248. Foot pedal 256 is a spring-biased analog pedal. A spring biases the foot pedal's upper surface upwards. As a user depresses the pedal upper surface, an analog signal is provided to electrical system 270. The magnitude of the analog signal is a function of the extent that user 210 has depressed pedal 256.

Six degree of freedom analog mouse 253 is also shown in FIG. 1. In this embodiment, mouse 253 may be a SpaceNavigator SE 3D model device offered from 3Dconnexion, of Fremont, Calif. User 210 may move mouse 253 within a limited space along the three translational axes (x, y, z) and may orient mouse 253 within a limited range in the roll, pitch, and yaw axes. The output from 6 DOF mouse 253 is provided to electrical system 270.

Digital button 254 is arranged on dental tool handle 242 and is used by electrical system 270 to initialize the position of virtual haptic tool 442 in virtual world 401.

As shown in FIG. 1, in this embodiment courseware computer 255 is a notebook computer arranged on the right side of platform 248 with a touch screen display. User 210 interacts directly with the touch screen display, touchpad, keyboard, speakers, and microphone of courseware computer 255.

Courseware computer includes software applications for: providing a training platform; providing instructional material and video; recording, replaying and evaluating a user's use of haptic interface 270; providing audio, visual and textual communication with a remote instructor over a computer network; providing a remote instructor ability to provide force inputs to haptic interface 230; and providing differing virtual objects, tools and physical rules into virtual environment 401.

As shown in FIG. 3, electrical system 270 is responsible for providing and receiving electrical signals with physical user interface 215. Signals coming out of electrical system include: stereo video signal, audio signal, and electrical drive lines to drive actuators A1, A2 and A3. Signals coming into electrical system 270 include: force sensor and position sensor signals from haptic dental drill handle 242; position and orientation sensor signals from dental mirror handle 250; position and orientation sensor signals from 6 DOF mouse 253; input signals from button 254; signals from foot pedal 256; and tachometer signals. Also, information is both provided and received from courseware computer 255.

Figure 8:
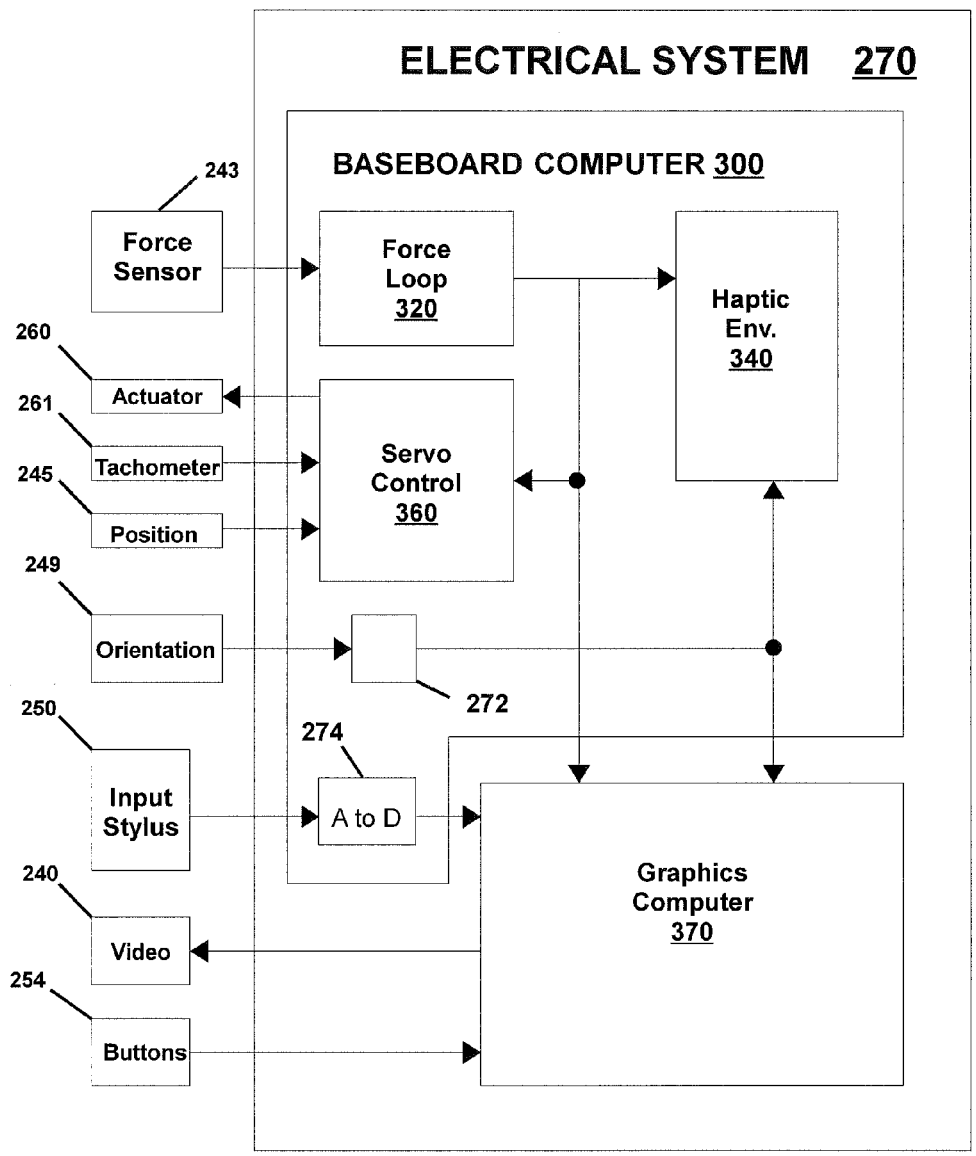
FIG. 8 is a system diagram of the electrical system shown in FIG. 3.

As shown in FIG. 8, electrical system 270 is made of baseboard computer or processor 300 and graphics computer or processor 370. Graphics computer 370's primary function is providing the audio and visual output signals to display 240 and speaker 241. Graphics computer 370 receives position and orientation input from 6 DOF mouse 253, dental mirror handle 250, and input button 254. Graphics computer 370 hosts the primary graphical portion of virtual environment 401. System 200's virtual environment 401 is generally a combination of both a graphical environment provided by graphics computer 370 and a haptic environment provided by baseboard computer 300.

Baseboard computer 300's primary function is maintaining the master variable for the position of virtual dental tool 442, and providing actuators A1, A2, A3 the necessary drive signals to cause the position of dental drill handle 242 to follow the position of virtual dental tool 442. Baseboard computer 300 receives haptic tool 242's force and orientation sensor signals and tachometer signals from physical user interface 215. As shown in FIG. 8, baseboard computer 300 includes force loop module 320, high frequency haptic virtual environment 340, and servo module 360. Force loop module 320 uses Newtonian physical algorithms to update virtual tool 442's position based upon the force signals received from dental drill handle 242, and an interaction force signal calculated by high frequency haptic virtual environment 340. Force loop 320 provides the calculated virtual dental tool 442 virtual position 327 to graphics computer 370, high frequency haptic virtual environment 340, and servo control module 360.

Servo control module 360 receives the virtual position 327 of virtual dental tool 442 and produces the proper drive signal to drive actuators A1, A2 and A3 to move dental drill handle 242 into the real world position correlating to virtual position 327 of virtual tool 442. Servo control module 360 uses the tachometer T1, T2, T3 signals and the dental drill handle position sensor 245 signals for feedback.

High frequency haptic virtual environment 340 calculates the interaction force to be applied to virtual dental tool 442 based on collisions between virtual dental tool 442 and other virtual objects in high frequency haptic virtual environment 340. As mentioned above, the position of virtual dental tool 442 is provided to haptic virtual environment 340 by force loop module 320. The three dimensional models of virtual objects are provided to haptic virtual environment 340 by graphics computer 370.

Figure 9:
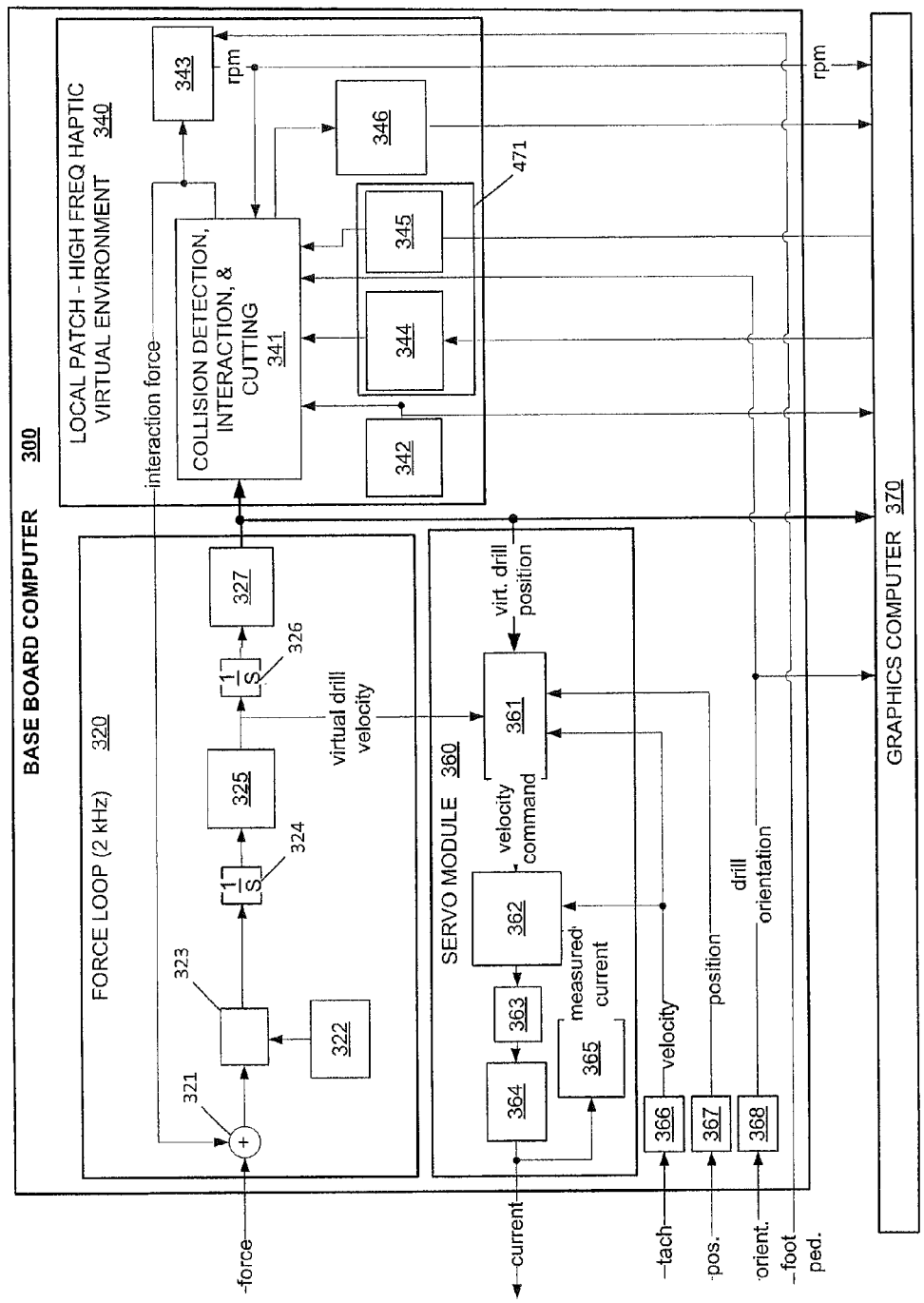
FIG. 9 is a system diagram of the base board computer shown in FIG. 8.

FIG. 9 shows a detailed system diagram of baseboard computer or processor 300. As mentioned above, baseboard computer 300 includes force loop module 320, high frequency haptic environment 340, and servo control module 360.

Force loop module 320 models the position of virtual dental tool 442 through an iterative process operating at a bandwidth of 2 kHz. A velocity variable 325 and a position variable 327 are iteratively adjusted by converting a force input into an acceleration and using the calculated acceleration to update the velocity and virtual drill position variables. More specifically, and as shown in FIG. 9, force loop 320 receives the three dimensional (x,y,z) haptic force signals from force sensors 243 in haptic tool interface 230 at a rate of 2 kHz. The haptic force signal is summed 321 with the three dimensional (x,y,z) interaction force received from high frequency haptic virtual environment 340. The summed force is divided 323 by virtual drill mass 322 to produce an acceleration. The acceleration is integrated 324 over time and used to adjust velocity variable 325. More specifically, $$\text{Velocity}_n = \text{Velocity}_{n-1} + \frac{\text{user applied force}}{\text{virtual mass}} \text{(iteration time unit)}$$

Velocity 325 is then integrated 326 over time and used to adjust virtual tool position variable 327, new position=old position+(velocity)×(time unit)

Velocity variable 325 is provided by force loop 320 to servo module 360. Virtual drill position variable 327 is provided to high frequency haptic virtual environment 340, servo module 360, and graphics computer 370.

Servo module 360 receives both the virtual drill velocity and virtual drill position from force loop 320. Servo module 360 uses the virtual drill velocity and position signals together with the tachometer 261 signals and drill handle position sensor 251 signals to produce drive signals for actuators A1, A2 and A3. The virtual drill position provided to servo module 360 is effectively a real world position command, which causes servo module 360 to drive actuators A1, A2 and A3 in order for the haptic tool handle to move to the commanded position.

More specifically, servo module 360 includes servo controller 361 operating at a rate of 2 kHz. Servo controller 261 receives the virtual drill velocity and position variables as well as the tachometer and drill handle position sensor signals converted from analog to digital by converters 366 and 367. Servo controller 361 uses a general PID (Proportional Integral Derivative) servo function to calculate the current command as a function of its inputs.

The current command is provided to FPGA current controller 362, which operates at 192 kHz. FPGA current controller outputs a modified current command adjusted based on measured current feedback provided from current sensor 365, as shown in FIG. 9. Current controller 362 uses a modified PID servo algorithm for producing its modified current command output. The modified current command is provided to digital to analog converter 363 and then directed to power amplifier 364. Power amplifier produces the drive signal that is provided to actuators A1, A2 and A3.

High frequency haptic virtual environment 340 ("HF haptic environment") includes the collision detection, interaction and cutting haptic engine 341, as well as an analytic model 342 for virtual drill 242 and drill model 343. A virtual object model 471 is provided from graphics computer 370. The virtual object (tooth) model 471 is made up of a virtual tooth local voxel patch 344 and a local tooth density map 345. HF haptic environment 340 also receives virtual drill position variable 327 from force loop 320, and dental drill handle 242's orientation from orientation sensors 244.

Collision detection, interaction and cutting haptic engine 341 determines the interaction force to be applied to virtual drill 442 based upon virtual drill position 327, virtual drill model 342, and virtual tooth model 371. Drill model 343 is also used to determine the next cutting position and orientation 346, which is provided to graphics computer 370. HF haptic environment 340 also uses drill model 343 to calculate the virtual drill RPM based upon the interaction force and foot pedal 256's position. The virtual drill rpm is then provided to haptic engine 341 and graphics computer 370.

The tooth model volume is represented as a set of three dimensional pixels, or voxels. Each voxel has a hardness value associated with it, representing the type/quality of tooth material (i.e. dentin, enamel, pulp). Also associated with each voxel is a color parameter and a warning level parameter. The warning level parameter is used by the software to aid in evaluating a student's performance. The conventional marching cubes algorithm is used to create a triangle mesh of an isosurface of the tooth model voxel set.

Unlike the tooth model, the virtual dental tool is modeled analytically. For example, a dental tool's spherical physical model is specified as a center point and a radius, or the equation:

$$x^2+y^2+z^2 \leq \text{radius}$$

Thus, the dental tool's physical model is not defined by a finite number of voxels, but rather by a complete analytically defined shape. The dental tool model also has a parameter for the tool model's virtual mass and a vector parameter for the tool model's three dimensional velocity.

Figure 10:
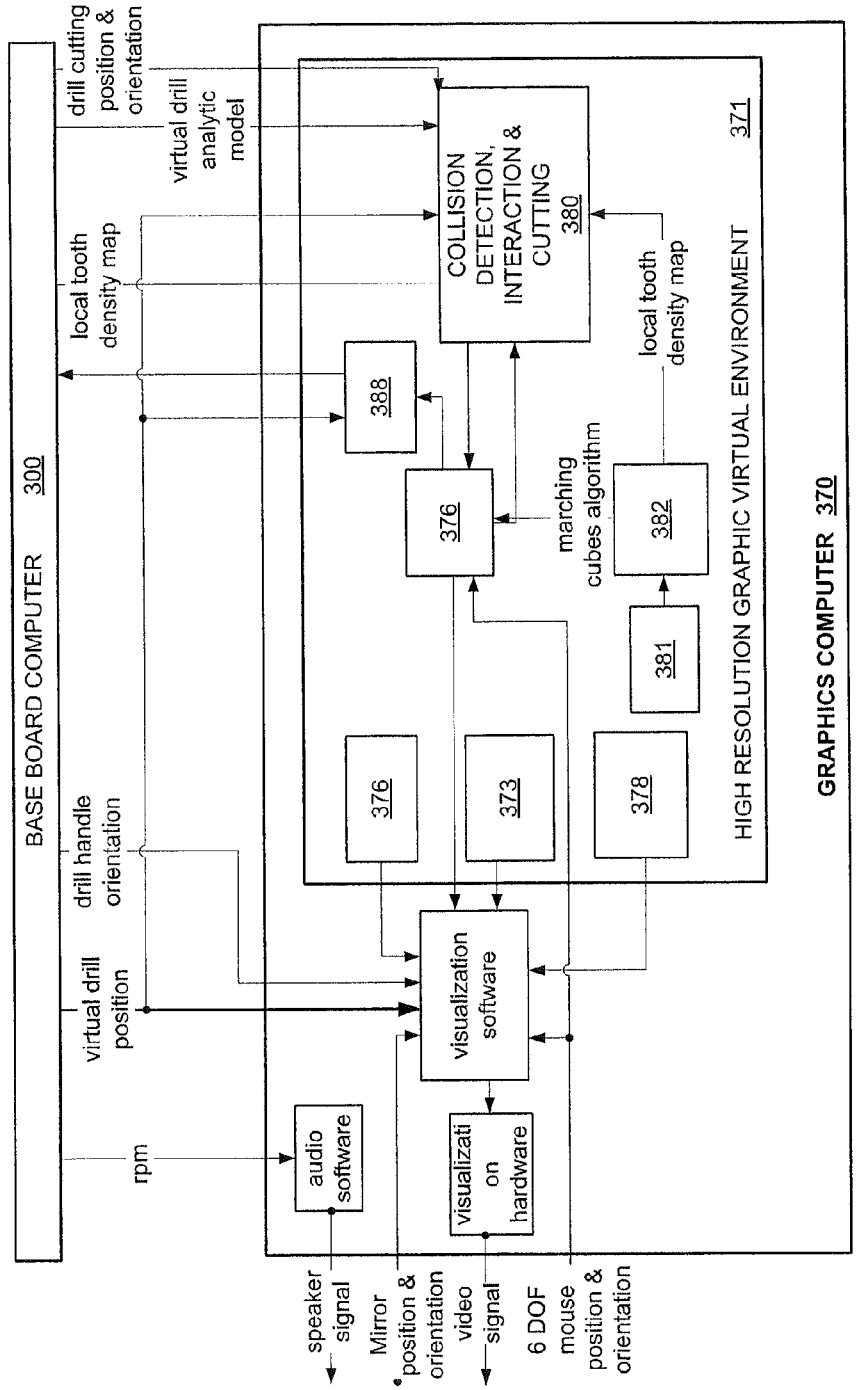
FIG. 10 is a system diagram of the graphics computer shown in FIG. 8.

A detailed system diagram of graphics computer 370 is shown in FIG. 10. As mentioned previously, graphics computer 370 provides the audio visual signals to display 240 and speaker 241. Graphics computer 370 receives the six degree of freedom position and orientation signals from haptic tool interface 230, dental mirror handle 250, and six DOF mouse 253. Virtual drill position 327 is received from baseboard computer 300.

As shown in FIG. 10, graphics computer 370 includes the primary components of high resolution graphic virtual environment 371, visualization software module 372, visualization hardware 373, and audio software 374. Audio software 374 receives the virtual drill rpm from drill RPM model 343 in baseboard computer 300 and provides an audio signal to speaker 241.

Graphic virtual environment 371 includes virtual drill triangular mesh 376, virtual dental mirror triangular mesh 377, virtual patient mouth triangular mesh 378, and virtual tooth triangular mesh 379. These triangular meshes are provided to visualization software 372. Visualization software 372 receives position and orientation signals for dental mirror handle 250, six DOF mouse 253, and the orientation signal for haptic dental drill handle 242. The position of dental drill handle 242 is not received by visualization software 372, rather, virtual drill position 327 is received from baseboard computer 300. Based on the received positions and orientations, visualization software 372 in conjunction with visualization hardware 373 produces the stereoscopic video signal provided to display 240.

Graphic virtual environment 371 also contains scanned tooth model 381 which is used to create virtual tooth voxel model 382. Collision detection interaction and cutting model 380 determines how to modify virtual tooth triangular mesh 379 based on the local tooth density map from tooth voxel model 382, virtual drill position 327, virtual drill analytic model 342, and drill cutting position and orientation 346. Collision detection, interaction, and cutting module 380 reproduces some of the haptic engine functions performed by baseboard computer 300's haptic engine 341. However, module 380 operates at a lower frequency and higher resolution than haptic engine 341. Module 380 also provides the local tooth density map to baseboard computer 300.

When beginning to use haptic user interface system 200, user 210 positions herself in a chair in front of system 200 and places shutter glasses 220 on. The chair height is properly selected to allow user 210 to puts her arms on arm rest 249. Courseware computer 255 is used to select a particular learning application or simulation environment. For example, user 210 may select a virtual dental surgery cavity drilling application and virtual environment. Courseware computer 255 will notify baseboard computer 300 and graphics computer 370 to load the appropriate information and variables for the selected application and environment. Graphics computer 370 will load the appropriate virtual models for virtual drill mesh, dental mirror mesh, and patient mouth mesh, and scanned tooth within high resolution graphic virtual environment 371. Baseboard computer 300 will similarly load the appropriate virtual drill analytic model, drill RPM model, and virtual drill mass. Virtual tooth model 471 is provided by graphics computer 370 to baseboard computer 300, and virtual drill analytic model 342 and the initial virtual drill position 327 are provided by baseboard computer 300 to graphics computer 370.

Graphics computer 370 begins providing stereoscopic display 240 with true to life scale images of the simulated surgery which user 210 will begin to see. Because user 210's left eye and right eye will receive separate views of the simulated surgery from perspectives separated by a typical eye to eye width, user 210 perceives a three dimensional view of the surgery. A virtual image of the dental mirror appears on the display in a co-located position with the real world dental mirror handle 250. In other words, as user 210 looks down at display 240, she sees the virtual dental mirror in the same position as the real dental drill handle 250 would appear if display 240 were not there. The convex lenses in shutter glasses 220 also cause user 210's eye lenses to focus to a depth consistent with the virtual images, adding to the realism of the system.

Graphics computer 370 calculates the appropriate image to display in the mirror portion of virtual dental mirror 450. As user 210 moves and reorients dental mirror handle 250, the virtual reflected image in the mirror portion of virtual mirror 450 is updated on display 240. This allows user 210 to view virtual tooth 471 in the same way that a real world dental mirror would be used to view a patient's teeth.

User 210 next presses button 254, which causes system 200 to initialize virtual drill position 327 to a starting position, which also causes the image of virtual drill 442 in display 240 to be co-located with real world position of dental drill handle 242.

User 210 places his/her foot on foot pedal 256. As foot pedal 256 is depressed, a modified signal is sent from foot pedal 256 to electrical system 270. The foot pedal signal is received by baseboard computer 300, and drill RPM model 343. Drill RPM model 343 determines the virtual drill rpm based upon the signal from foot pedal 256. The rpm is provided to graphics computer 370, in which audio software 374 determines the audio signal to be sent to speaker 241. Speaker 241 generates a sound characteristic of a dental drill for the given rpm which is heard by user 210. Since speaker 241 is located close to dental drill handle 242, user 210 perceives the sound as coming from the location of virtual drill 442 that she sees in display 240.

High frequency haptic virtual environment 341 is constantly comparing the relative positions of virtual drill 442 and the surface points of virtual object 471. More specifically, haptic engine 380 will use the iterative algorithm shown in FIG. 11 to calculate collisions and interaction forces. Haptic virtual environment 371 receives a subset voxel volume of virtual tooth model in close proximity to the virtual drill position 327. As shown in FIG. 9, this limited voxel volume is virtual tooth local voxel patch 344. Haptic virtual environment 371 is also provided a map 345 containing a hardness value and stiffness value for each voxel of the virtual tooth local patch 344.

Figure 11:
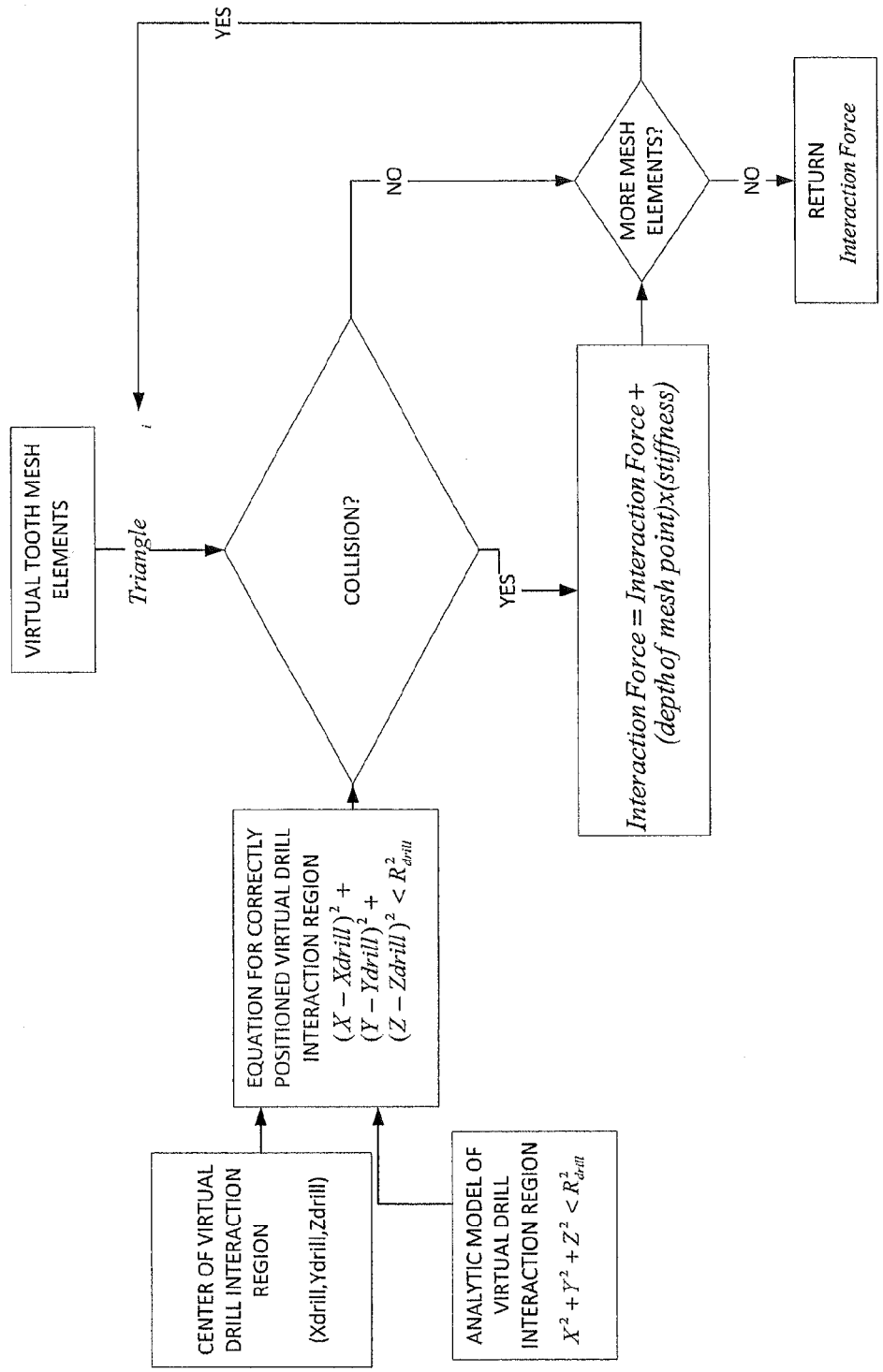
FIG. 11 is a flowchart of the interaction force calculation algorithm.

The algorithm in FIG. 11 demonstrates how each of the verticies in a surface mesh created from virtual tooth local voxel patch 344 is tested for collision with the virtual drill interaction region. Each time a collision is detected between a tooth mesh vertex and the virtual drill interaction region, an interaction force component is calculated. The interaction force component is proportional to the product of the depth the vertex has collided into the virtual drill interaction region, and the stiffness assigned to the vertex element. Because each tooth voxel element may have its own hardness and stiffness value, the virtual environment is able to more realistically simulate different tooth materials, such as dentin, enamel, pulp and cavity. All interaction force components of each colliding vertex is summed to create a total interaction force which is provided to force loop 320 to apply to virtual drill mass 323.

The collision detection, interaction and cutting engine 341 also calculates how much volume should be removed from virtual tooth 471 during a collision. The volume of virtual tooth removed is a function of the drill rpm received from drill RPM model 343 and the calculated interaction force. The faster the drill rpm and the higher the interaction force, the more virtual tooth volume that will be removed over time. The virtual tooth model is constantly updated as its volume is changed.

During the simulation process, user 210 may use six DOF mouse 253 to adjust the camera view of the virtual environment displayed in display 240. The environment may be tilted in three degrees of freedom and panned in two degrees of freedom. Additionally, the last degree of freedom is used to zoom in or out.

Courseware computer 255 records the haptic forces applied by the user, the motions of the virtual tools 442 and 450, and the modifications made to virtual tooth 471. Either user 210 or an instructor can playback the virtual session in order to review or evaluate user 210's performance. Additionally, courseware computer 255 may automatically produce a performance score based on the user's performance. For example, courseware computer 255 will compare the volume elements of tooth removed with volume elements of cavity and healthy tooth material.

Additionally, a network connection through courseware computer 255 allows an instructor to remotely monitor user 210's performance, and offer live feedback via audio speaker 241, visual display 240, or courseware computer 255.

Other embodiments of the haptic user interface system may be implemented to simulate environments other than dental surgery. For example, virtual dental drill and virtual mirror may be replaced with a virtual scalpel and forceps for heart surgery. The haptic tool may represent a flight control stick for aircraft flight simulation. Other virtual reality type environments, such as for gaming, may also be implemented.

In other embodiments, different three dimensional technologies other than the eclipse/shutter glasses method may be used. For example, linearly polarized glasses in which the left and right lenses are mounted with perpendicular polarizations may be used in concert with a display that projects the left and right images simultaneously with different linear polarizations. Alternatively, a visual display with a lenticular lens system can be used to project 3D images without user 210 having to wear special glasses.

Other embodiments may have a speaker positioned inside the dental drill handle. Additionally, vibration actuators, such as unbalanced mini-motors or piezoelectric actuators, may be used to provide additional vibration feedback to user 210. Such vibrations could be applied to simulate the vibration of a dental drill, or the jolt of collisions between tools and solid objects.

Rather than using an input button to zero the virtual haptic tool position, another embodiment may use the haptic tool position sensors to slowly correct for drift. If the real world position of the haptic tool handle is used to provide a feedback with a very low update rate (low feedback constant), the "force-in-position-out" haptic engine operating paradigm, with all its advantages, would still operate correctly without introducing feedback instabilities, and virtual haptic tool drift would be minimized.

Other embodiments may have two haptic tools, one for each hand. Various alternative collision algorithms and physical operating laws may be used. For example, the simulation may take place in slow motion, or in Martian gravity.

In other embodiments, the network connection through the courseware computer may be used to provide haptic control to a remotely located surgical robot. Similarly, two haptic user interface systems may be networked together, such that one user may provide "hands on" guidance to the other user. For example, an unstructor may show technique by example on the user's display.

The single speaker may be replaced with a 3D speaker system to provide additional realism in various environments.

The non-haptic tool, such as the dental mirror handle, may be implemented with wireless technology and embedded gyroscopes and accelerometers in order to provide greater mobility and range of motion.

The display may be a head mounted display, with motion tracking, to further add to the realism of the user interface system.

The described user interface resulted in several surprising advantages over the prior art. Large force interactions between the haptic tool and virtual objects is superiorly modeled with the described force-in-position-out method over prior art systems using position-in and force feedback. In order to model a near infinitely stiff (hard) surface, a position-in force feedback system will need to have extremely high position sensing resolution and extremely high bandwidth in the haptic engine in order to accurately calculate and apply the correct feedback force.

In contrast, the present system does not need to have as high resolution position or force sensors to model near infinitely stiff surfaces accurately, nor does it need to have a haptic rendering engine running at a very high frequency. By splitting the feedback into multiple loops, the present system only uses high frequency hardware (192 KHz) for the position feedback loop. The haptic engine only needs to provide moderate bandwidth (2 KHz). A higher bandwidth is not needed to simulate hard surfaces, because if a user applies forces to the haptic handle at a bandwidth higher than the haptic engine (2 KHz), the inherent stiffness of the mechanical structure of the haptic interface provides the appropriate reaction force to the user. In other words, because a multiplication with a close to infinite stiffness variable does not have to be performed in calculating a feedback, lower resolution sensors and lower bandwidth hardware can achieve similar results at modeling a hard surface than a position-in force feedback system. Additionally, with equivalent bandwidth hardware and sensors, the presently described force-in-position-out system will provide much superior modeling of hard surfaces over position-in force feedback systems.

The ability to have lower frequency force sensing and haptic engine loops is especially attractive in telemedicine or remote type setups where network latency may limit the feedback bandwidth. For example, the present system may be used for remote dental surgery, with a dentist on the presently described haptic user interface, connected to a robotic drill and patient at a remote location. The high frequency position feedback loop runs locally on servo module 360 (FIG. 9). In other words, the position feedback signals from position sensors 367 are provided to servo module 360 and the corrective response is provided from servo module 360 to the haptic actuatators; the position signal does not need to be provided at a high frequency to a remote control location. Thus the position command, sent from the robotic drill to the doctors haptic user interface, only needs to be sent at a frequency of 2 KHz, the haptic engine bandwidth. The ability to not have to send commands between the virtual drill and remote haptic user interface at high frequencies is especially advantageous since remote network connections often have significant latency. In such a telesurgery setup, a position-in force feedback prior art system would have difficulty obtaining the necessary network bandwidth and latency in order to accurately recreate the high forces of interacting with hard surfaces such as teeth.

The co-located stereoscopic display also results in unprecedented realism which improves the efficiency of training.

While an embodiment of the haptic user interface has been shown and described, and several modifications thereof discussed, persons skilled in this art will readily appreciate that various additional changes may be made without departing from the scope of the invention.

The invention claimed is:

1. A method of simulating a virtual procedure comprising the steps of:
   providing a user interface having a user connection element with at least three independent translational degrees of freedom between said user connection element and a reference;
   said user interface comprising three force sensors for measuring forces applied to said user interface along said three independent translational degrees of freedom and three actuators for controlling each of said three independent translational degrees of freedom;

providing a video display arranged to produce a stereoscopic view co-located with said user connection element;

providing a three dimensional virtual environment comprising a virtual element having a virtual position and at least one virtual object having a virtual position;

adjusting said virtual position of said virtual element as a function of said user interface force sensors;

said step of adjusting said virtual position of said virtual element as a function of said user interface force sensors comprising the steps of assigning a virtual mass to said virtual element, receiving output from said user interface force sensors, providing an acceleration variable of said virtual element within said virtual environment as a function of said output from said user interface force sensors and said virtual mass of said virtual element, integrating said acceleration variable to provide a velocity variable of said virtual element within said virtual environment, and integrating said velocity variable to provide a virtual position of said virtual element within said virtual environment;

controlling said actuators such that said user connection element is adjusted to correlate to changes in said virtual position of said virtual element; and providing said video display with images of said virtual environment.

2. The method set forth in claim 1, wherein said virtual object comprises a triangular mesh.

3. The method set forth in claim 1, wherein said virtual element comprises an interaction region defined by an analytic function.

4. The method set forth in claim 3, and comprising the step of detecting a collision between said virtual element interaction region and said virtual object.

5. The method set forth in claim 4, and comprising the step of calculating an interaction force as a function of said collision and accelerating said virtual element as a function of said interaction force.

6. The method set forth in claim 5, and comprising the step of modifying said virtual object as a function of said collision.

7. The method set forth in claim 1, where said user connection element has three independent orientation degrees of freedom between said user connection element and said reference, said user interface has three orientation sensors for measuring said three independent orientation degrees of freedom, said virtual element has a virtual orientation, and said virtual object has a virtual orientation.

* * * * *